(12) United States Patent
Haselton et al.

(10) Patent No.: US 10,190,114 B2
(45) Date of Patent: Jan. 29, 2019

(54) LOW RESOURCE SAMPLE PROCESSOR CONTAINING HEAT-ACTIVATED SURFACE TENSION VALVES

(71) Applicant: Vanderbilt University, Nashville, TN (US)

(72) Inventors: Rick Haselton, Nashville, TN (US); Nick Adams, Nashville, TN (US)

(73) Assignee: VANDERBILT UNIVERSITY, Nashvile, TN (US)

( * ) Notice: Subject to any disclaimer, the term of this patent is extended or adjusted under 35 U.S.C. 154(b) by 583 days.

(21) Appl. No.: 14/835,328

(22) Filed: Aug. 25, 2015

(65) Prior Publication Data

US 2016/0054207 A1  Feb. 25, 2016

Related U.S. Application Data

(60) Provisional application No. 62/041,195, filed on Aug. 25, 2014.

(51) Int. Cl.
| | |
|---|---|
| G01N 1/34 | (2006.01) |
| C12N 15/10 | (2006.01) |
| G01N 1/44 | (2006.01) |
| B01L 3/00 | (2006.01) |
| B01L 7/00 | (2006.01) |
| C12Q 1/6806 | (2018.01) |

(52) U.S. Cl.
CPC .... *C12N 15/1013* (2013.01); *B01L 3/502761* (2013.01); *B01L 7/525* (2013.01); *C12Q 1/6806* (2013.01); *G01N 1/44* (2013.01); *B01L 7/5255* (2013.01); *B01L 2200/0673* (2013.01); *B01L 2300/087* (2013.01); *B01L 2300/0838* (2013.01); *B01L 2400/043* (2013.01); *B01L 2400/0409* (2013.01); *B01L 2400/0677* (2013.01); *B01L 2400/0688* (2013.01)

(58) Field of Classification Search
CPC ......... B01L 2400/043; B01L 3/502738; B01L 2200/0647; B01L 2400/0688; B01L 2200/10; B01L 2300/0816; B01L 2300/161; B01L 3/502761; B01L 2200/0668; B01L 2300/0838; B01L 2300/087; B01L 2400/0677
See application file for complete search history.

(56) References Cited

U.S. PATENT DOCUMENTS

| | | | |
|---|---|---|---|
| 2010/0273142 A1* | 10/2010 | Prins ................. | B01L 3/502738 435/4 |
| 2012/0077260 A1* | 3/2012 | Sharon ............... | B01L 3/502738 435/287.2 |
| 2012/0126154 A1* | 5/2012 | Den Dulk .......... | B01L 3/502738 251/11 |

FOREIGN PATENT DOCUMENTS

WO  WO 2012009627 A2 *  1/2012  ........ B01L 3/502738

OTHER PUBLICATIONS

Chen et al., "An integrated, self-contained microfluidic cassette for isolation, amplification, and detection of nucleic acids", *Biomed. Microdevices*, 12(4):705-719, 2010.

(Continued)

*Primary Examiner* — Erik B Crawford
(74) *Attorney, Agent, or Firm* — Parker Highlander PLLC

(57) ABSTRACT

Systems and methods are described for isolation, separation and detection of a molecular species using a low resource device for processing of samples. Methods include isolation, separation and detection of whole cells as well as biomolecules including viruses, proteins, nucleic acids, carbohydrates and lipids.

18 Claims, 14 Drawing Sheets

Specification includes a Sequence Listing.

(56) References Cited

OTHER PUBLICATIONS

Hagan et al., "An integrated, valveless system for microfluidic purification and reverse transcription—PCR amplification of RNA for detection of infectious agents", *Lab. Chip.*, 11(5):957-961, 2011.
Niemz et al., "Point-of-care nucleic acid testing for infectious diseases", *Trends Biotechnol.*, 29(5):240-250, 2011.
Price et al., "Nucleic acid extraction techniques and application to the microchip", *Lab. Chip.*, 9(17):2484-2494, 2009.

* cited by examiner

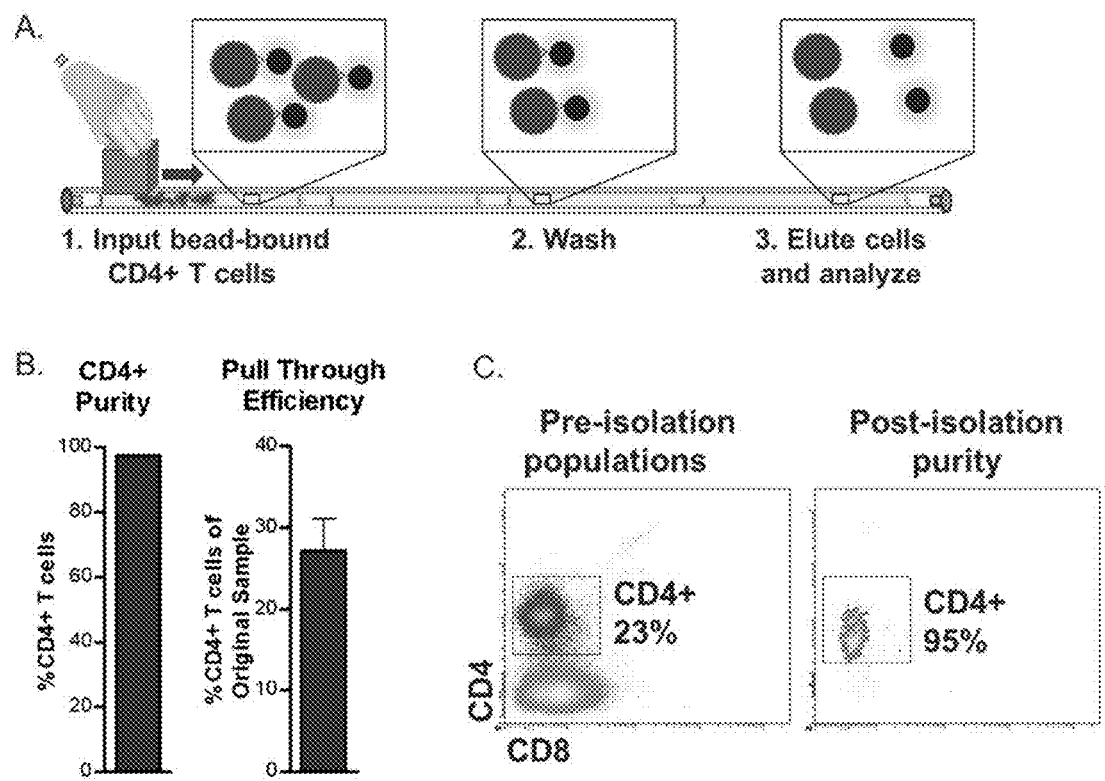
FIGS. 9A-C

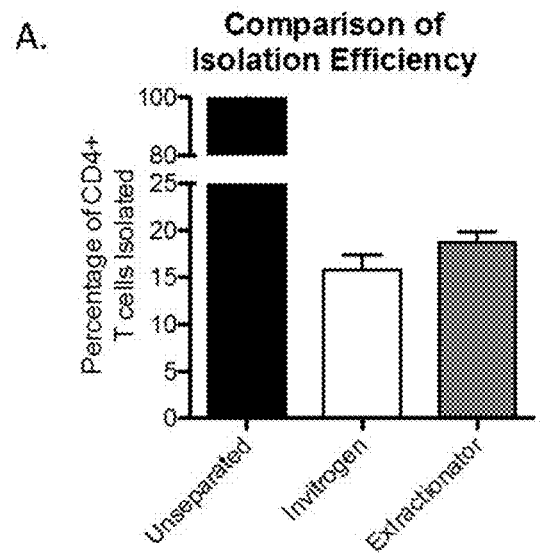
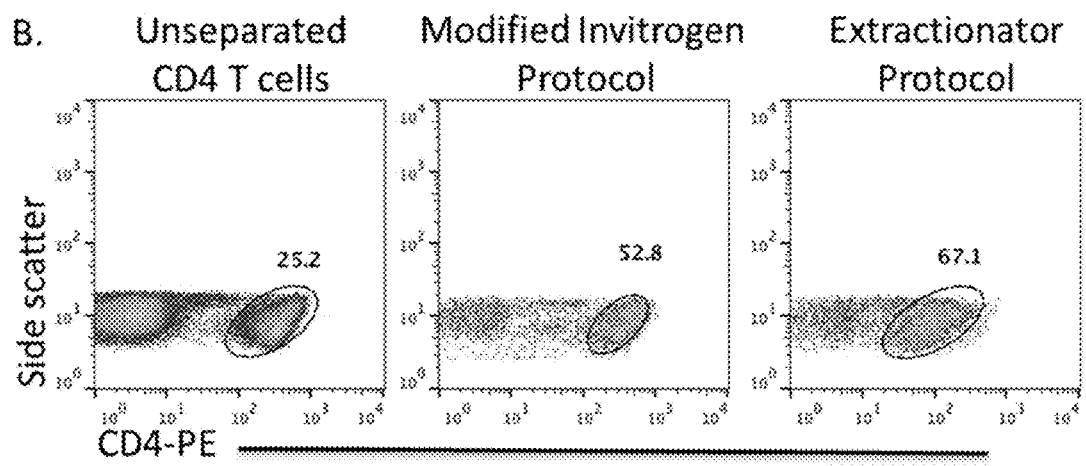
FIGS. 10A-B

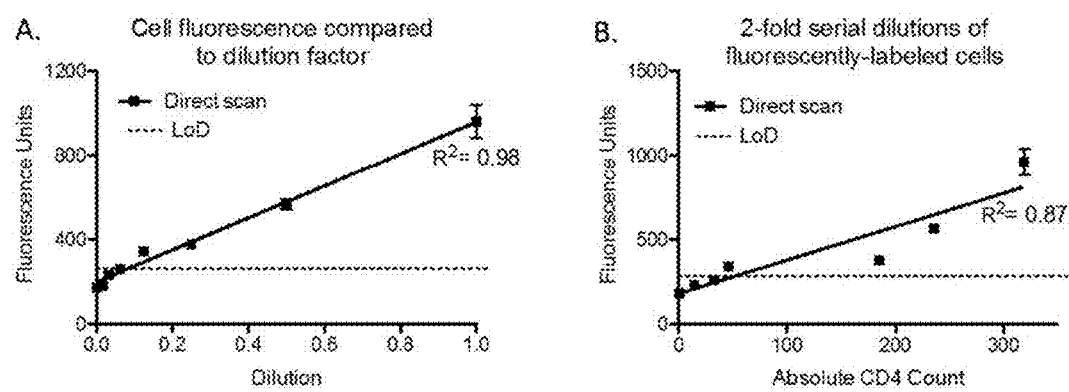
FIGS. 11A-B

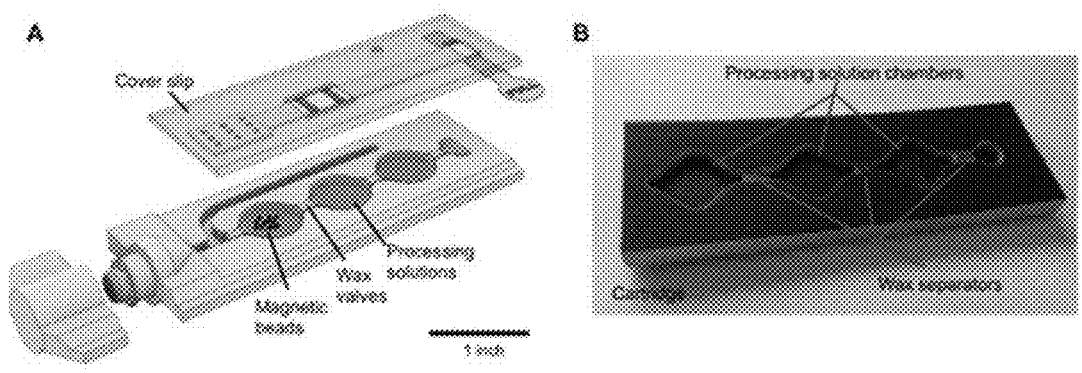
FIGS. 14A-B

LOW RESOURCE SAMPLE PROCESSOR CONTAINING HEAT-ACTIVATED SURFACE TENSION VALVES

This application claims benefit of priority to U.S. Provisional Application Ser. No. 62/041,195, filed Aug. 25, 2014, the entire contents of which are hereby incorporated by reference.

The invention was made with government support under Grant No. DGE 0909667 awarded by the National Science Foundation. The government has certain rights in the invention.

BACKGROUND

The sequence listing that is contained in the file named "VBLTP0240US_ST25.txt", which is 1 KB (as measured in Microsoft Windows®) and was created on Oct. 10, 2018, is filed herewith by electronic submission and is incorporated by reference herein.

1. Field of the Disclosure

The disclosure relates generally to the field of diagnostics and detection. More particularly, the disclosure relates to low resource processors for assessing molecular interactions. Specifically, the disclosure relates to the use of devices containing multiple chambers separated by heat activated surface tension valves for the processing of microbeads having detection and/or screening reagents attached thereto. The device permits assaying for the content of a wide variety of environmental and biological samples, including those containing whole cells or biological or chemical materials.

2. Description of Related Art

Recent research has focused on the development of nucleic acid-based detection for low resource settings (Niemz et al., 2011). Nucleic acid-based detection systems, such as quantitative PCR (qPCR), are particularly attractive technologies for detection of pathogens because of their sensitivity, specificity and relatively rapid time-to-answer. The effectiveness of PCR is dependent on both the quality and quantity of nucleic acid template (Beuselinck et al., 2005) and the absence of interferents (Radstrom et al., 2004). For example, carbohydrates, proteins, lipids or other unidentified interferents present in clinical samples have all been shown to inhibit PCR and produce false negatives (Monteiro et al., 1997; Wilson, 1997; Coiras et al., 2003). In addition to various interferents, patient samples also contain nucleases, which directly reduce the number of nucleic acid targets present (Wilson, 1997).

To minimize false negatives and maximize the efficiency of nucleic acid-based diagnostics, nucleic acids are extracted and concentrated into an interferent-free buffer prior to testing. Several solid phase extraction kits are commercially available to purify DNA or RNA from patient samples. Many of these kits rely on selective nucleic acid binding to silica-coated surfaces in the presence of ethanol and a chaotropic agent, such as guanidinium thiocyanate (GuSCN) (Avison, 2007; Yamada et al., 1990). These kits are not cost effective for low resource use and often require the use of specialized laboratory equipment, such as a robot or centrifuge, and trained technicians that are unavailable in a low resource setting.

Microfluidics is one promising format for low resource cell-based diagnostics. Recently, there has been a growing interest in expanding microfluidic technologies for sample preparation (Niemz et al., 2011; Price et al., 2009). Many of these devices are suitable for integrating with downstream nucleic acid amplification and detection technologies (Chen et al., 2010; Hagan et al., 2011). However, the small surface area of solid phase available for cell binding and the limited sample volume that can be flowed through the channels limit the total mass of material recovered (Niemz et al., 2011), and therefore negatively impact the limit of detection.

Similar issues relate to the testing for many species of interest, including proteins, lipids, carbohydrates, and whole cells. Therefore, a rapid, noninvasive diagnostic technology for the isolation of whole cells is desirable, especially in low resource environments. Such technology would allow for blood cell profiling and the isolation and detection of cells to aid in cancer detection and to monitor disease progression and response to therapy for diseases such as HIV.

SUMMARY

Thus, in accordance with the present disclosure, there is provided a method of processing an analyte-containing sample comprising (a) providing a device comprising a plurality of sequential chambers connected by tubing, each of said sequential chambers comprising a fluid and separated by plug material that is solid at temperatures below 45° C. to 60° C., wherein a first reaction chamber comprises a particle having a reactant on its surface; (b) introducing into said first reaction chamber a sample comprising an analyte; (c) incubating said first reaction chamber under conditions sufficient to permit reaction of said reactant with said analyte in said sample; (d) subjecting said plug material in said device to a temperature above 45° C. to 60° C., thereby rendering at least a portion of said plug material into a liquid state, thereby forming a surface tension valve; (e) transporting said particle from said first reaction chamber into at least a second chamber through tubing disposed therebetween; and (f) detecting interaction of said analyte with said reactant.

The device may comprise at least three chambers, such as a said first reaction chamber, a first processing chamber and a first detection chamber, wherein said first processing chamber is disposed between said first reaction chamber and said first detection chamber. The method may further comprise reversing the transport of said particle to reintroduce said particle into a chamber through which it has already passed. The device may comprise continuous tubing and multiple plugs separating said tubing into said plurality of chambers. The tubing may be made of glass, a polymer or a metal. The tubing may comprise an inner surface coated by a polymer. The particle may be a magnetic particle, a paramagnetic particle or a non-magnetic particle having a relative density of >1 or <1 compared to the reaction chamber fluid, and transporting may comprise passing a magnetic field along said tubing or subjecting said tubing to distinct intermittent magnetic fields to effect movement of said particle. Transporting may also comprise applying centrifugal or gravitational force to said device such that said particle is transported through said plurality of chambers. The non-magnetic particle may have a relative density of >1 compared to the reaction chamber fluid is transported by density driven transport.

The analyte may be a whole cell (such as a protist, an animal cell, a plant cell, a fungal cell, a bacterial cell), a protein, a polypeptide, a lipid, a carbohydrate, a nucleic acid, a heavy metal, an organochemical compound, a virus, a metabolite, a toxin, or a drug. The protist may be of the genus *Plasmodium, Babesia, Leishmania, Giardia*, or *Trypanosoma*. The animal cell may be a mammalian cell. The reactant may be an antibody, an aptamer, or a cell surface receptor ligand. Detecting interaction of said analyte with said reactant may comprise FRET, colorimetric assay, fluorescence assay, RT-PCR, change in optical density, or change in refractive index. Introducing may comprise injecting said sample through a wall of said first reaction chamber, or may comprise movement of said sample into said first reaction chamber by capillary action. The sample may be a biological sample, such as a tissue or fluid sample obtained from a patient, or an environmental sample, such as a soil sample, a water sample, or a plant sample.

The particle may be is 0.1 to 10 micrometers in diameter. The tubing may be 0.5 to $10^4$ micrometers in diameter. The tubing may have a diameter of 3/16 of an inch, or a cross section of 0.028 sq.inches. The plug material may be a alkane having between 28 and 42 carbons. The plug material may have a melting point of 61° C. to 95° C. The plug material may be a paraffin wax, petroleum jelly, polyethylene wax, ester-containing alkyl chains, carboxylic acid-containing alkyl chains, alcohol-containing alkyl chains (e.g., lanolin, bees wax).

The first reaction chamber may further comprise a known quantity of control analyte. The sample may be spiked with a known quantity of control analyte. The method may further comprise quantifying the amount of analyte in the original sample by calculating the processing efficiency of the method using the known quantity of control analyte. The method may further comprise a multiplex detection method, wherein said first reaction chamber further comprises a second particle having a second reactant on its surface, said sample further comprises a second analyte, said incubating further permits reaction of said second reactant with said second analyte, and said detecting further detects interaction between said second reactant and said second analyte, where the second analyte may be a whole cell (such as a protist, an animal cell, a plant cell, a fungal cell, a bacterial cell), a protein, a polypeptide, a lipid, a carbohydrate, a nucleic acid, a heavy metal, an organochemical compound, a virus, a metabolite, a toxin, or a drug. The protein may be an antigen, an antibody, or an enzyme. The second reactant may be an antibody, an antigen, a chelating agent, a lipid, a carbohydrate, a metal, an organochemical compound, an enzyme substrate, a nucleic acid, or a second cell. Detecting interaction of said second analyte with said second reactant may comprise FRET, colorimetric assay, fluorescence assay, spectrophotometry, RT-PCR, change in optical density, or change in refractive index.

Step (d) may take place after step (a) but before step (b), or after step (b) but before step (c), or after step (c). Step (d) may comprise subjecting all of said device to a temperature above 45° C. to 60° C., or a portion of said device to a temperature above 45° C. to 60° C. Step (d) may comprise blowing heated forced air across all or a portion of the surface of said device. Step (d) may comprise inserting all or a portion of said device into a chamber or machine that heats said device. Step (d) may comprise contacting all or a portion of said device with a heated objected. Step (d) may comprise applying a heated magnet or a heated element affixed to a magnet to said device. Upon heating, the plug material may be only partially liquefied. The plug material may comprise reactants that, following heating and melting, form a permanent plug that is resistant to melting at temperatures of 45-60° C., 45-100° C. or 60-100° C.

In another embodiment, there is provided a method of processing an analyte-containing sample comprising (a) providing a device comprising a plurality of sequential chambers connected by tubing, each of said sequential chambers comprising a fluid and separated by a plug material that is solid at a temperature of less than 45° C. to 60° C.; (b) introducing into said first chamber a particle comprising a surface reactant, the surface of which comprises an analyte bound to said reactant; (c) subjecting said plug material in said device to a temperature above 45° C. to 60° C., thereby rendering at least a portion of said plug material into a liquid state, thereby forming a surface tension valve; (d) transporting said particle from said first chamber into at least a second chamber through tubing disposed therebetween; and (e) detecting the presence of said analyte. The method may further comprise mixing said particle with a sample to permit binding of said analyte to said reactant on said particle. The particle may be a magnetic particle, a paramagnetic particle or a non-magnetic particle having a relative density of >1 or <1 compared to the reaction chamber fluid, and transporting may comprise passing a magnetic field along said tubing or subjecting said tubing to distinct intermittent magnetic fields to effect movement of said particle. The non-magnetic particle may have a relative density of >1 compared to the reaction chamber fluid is transported by density driven transport. Transporting may comprise applying centrifugal force to said device such that said particle is transported through said plurality of chambers.

The analyte may a whole cell (such as a protist, an animal cell, a plant cell, a fungal cell, a bacterial cell), a protein, a polypeptide, a lipid, a carbohydrate, a nucleic acid, a heavy metal, an organochemical compound, a virus, a metabolite, a toxin, or a drug. The protist may be of the genus *Plasmodium, Babesia, Leishmania, Giardia,* or *Trypanosoma*. The animal cell may be a mammalian cell. The reactant may be an antibody, an aptamer, or a cell surface receptor ligand. Detecting interaction of said analyte with said reactant may comprise FRET, colorimetric assay, fluorescence assay, RT-PCR, change in optical density, or change in refractive index. Introducing may comprise injecting said particles through a wall of said first chamber, or may comprise movement of said sample into said first reaction chamber by capillary action. The sample may be a biological sample or environmental sample, such as a tissue or fluid sample obtained from a patient, or an environmental sample, such as a soil sample, a water sample, or a plant sample.

The device may comprise at least three chambers, such as a first reaction chamber, a first processing chamber and a first detection chamber, wherein said first processing chamber is disposed between said first reaction chamber and said first detection chamber. The method may further comprise reversing the transport of said particle to reintroduce said particle into a chamber through which it has already passed. The plug material may be a alkane having between 28 and 42 carbons. The plug material may have a melting point of 61° C. to 95° C. The plug material may be a paraffin wax, petroleum jelly, polyethylene wax, ester-containing alkyl chains, carboxylic acid-containing alkyl chains, alcohol-containing alkyl chains (e.g., lanolin, bees wax). The first reaction chamber may further comprise a known quantity of control analyte, or the surface in step (b) may further comprise a known quantity of control analyte. The method may further comprise quantifying the amount of analyte in the original sample by calculating the processing efficiency of the method using the known quantity of control analyte.

The method may further comprise a multiplex detection method, wherein said first reaction chamber further comprises a second particle having a second reactant on its surface, said sample further comprises a second analyte, said incubating further permits reaction of said second reactant with said second analyte, and said detecting further detects interaction between said second reactant and said second analyte. The second analyte may be a whole cell (such as a protist, an animal cell, a plant cell, a fungal cell, a bacterial cell), a protein, a polypeptide, a lipid, a carbohydrate, a nucleic acid, a heavy metal, an organochemical compound, a virus, a metabolite, a toxin, or a drug. The protein may be an antigen, an antibody, or an enzyme. The second reactant may be an antibody, an antigen, a chelating agent, a lipid, a carbohydrate, a metal, an organochemical compound, an enzyme substrate, a nucleic acid, or a second cell. Detecting interaction of said analyte with said second reactant may comprise FRET, colorimetric assay, fluorescence assay, spectrophotometry, RT-PCR, change in optical density, or change in refractive index.

Step (c) may takes place after step (a) but before step (b), or after step (b). Step (c) may comprise subjecting all of said device to a temperature above 45° C. to 60° C., or a portion of said device to a temperature above 45° C. to 60° C. Step (c) may comprise blowing heated forced air across all or a portion of the surface of said device. Step (c) may comprise inserting all or a portion of said device into a chamber or machine that heats said device. Step (c) may comprise contacting all or a portion of said device with a heated objected. Step (c) may comprise applying a heated magnet or a heated element affixed to a magnet to said device. Upon heating, the plug material may be only partially liquefied. The plug material may comprise reactants that, following heating and melting, form a permanent plug that is resistant to melting at temperatures of 45-60° C., 45-100° C. or 60-100° C.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 9A-C—CD4+ T cell extraction. (FIG. 9A) Diagram of the extraction method and device. (FIG. 9B) Quantification of the CD4+ T cell purity and pull through efficiency. (FIG. 9C) FACS analysis of the pre-isolation populations and post-isolation purity.

FIGS. 10A-B—CD4 extraction: high isolation efficiency versus standard separation protocol. (FIG. 10A) Comparison of isolation efficiency. (FIG. 10B) Comparison of isolation purity. Gated percentages indicate percent CD4+ T cells of parent lymphocyte gate.

FIGS. 11A-B—Enumeration of fluorescently-labeled cells using a spectrophotometer. PBMC were labeled with anti-CD4-PE antibodies and 2-fold serial dilutions were prepared. Cells were counted using flow cytometry and total fluorescence was measured on a laboratory spectrophotometer. (FIG. 11A) Linear regression of the 2-fold serial dilution vs. fluorescence. (FIG. 11B) Linear regression of the cell count versus fluorescence.

FIGS. 14A-B—Example of a processing cartridge design using wax barriers to separate processing solutions. (FIG. 14A) Wax barriers (yellow) separate processing solutions (blue and orange) and with the cover slip applied to seal the top, they prevent the processing solutions from mixing during storage, shipping, and handling. (FIG. 14B) Image of a plastic cartridge containing wax separators prior to the addition of the processing solutions and cover slip.

DESCRIPTION OF ILLUSTRATIVE EMBODIMENTS

Figure 1:
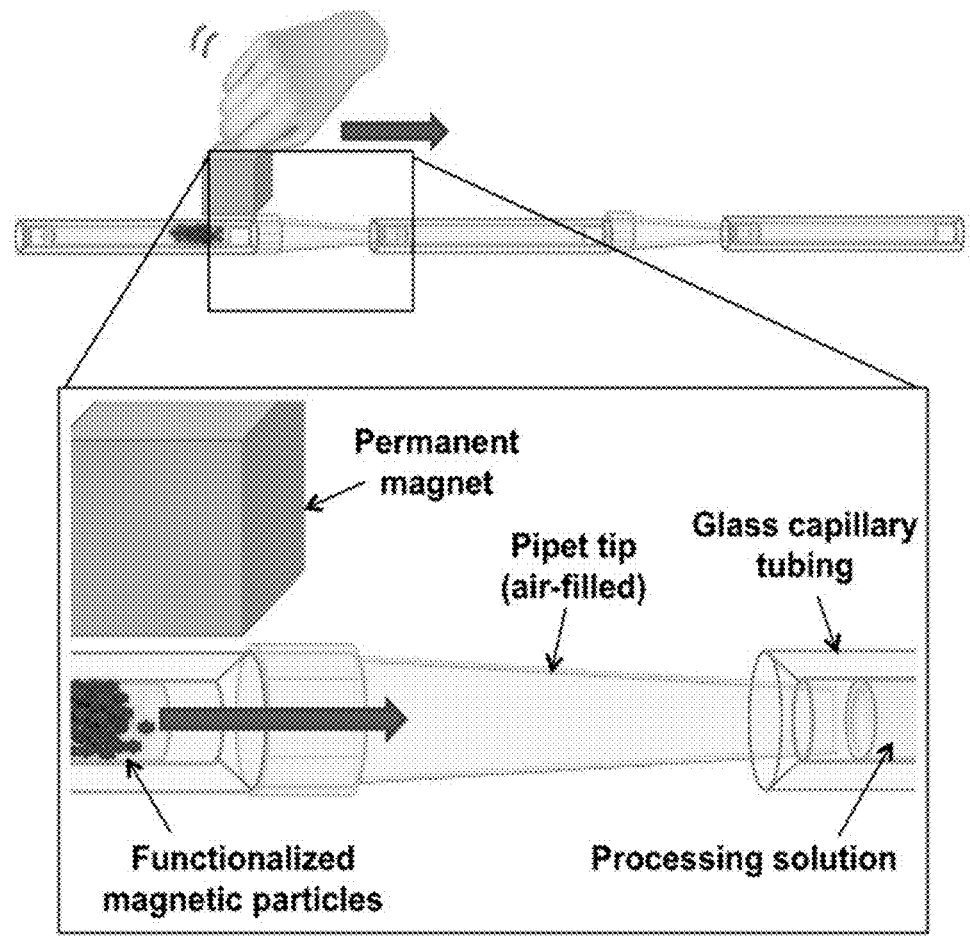
FIG. 1—Design of the prototype extraction method showing three processing solutions held in place in glass tubing and separated by air-filled pipette tips. RNA is adsorbed to silica-coated magnetic particles which are pulled left to right through successive processing chambers using an external magnet. Following processing, the RNA is eluted in a final water chamber.

In previous studies, the inventors developed an alternative whole cell extraction cassette suitable for operation in a low resource setting. This self-contained extraction cassette is preloaded with processing solutions separated by air gaps, which are referred to as "surface tension valves." In whole cell extraction studies, CD4+ T cells are selectively adsorbed to antibody-coated magnetic particles. Individual processing solutions are preloaded into a single continuous length of Tygon tubing and are separated from one another and held in place by surface tension forces. Removal of non-target cells is achieved by selective CD4 adsorption to antibody-coated magnetic particles which are then pulled through each processing solution using an externally applied magnetic field. CD4+ T cells are eluted from the surface of the magnetic particle in the final solution. This report describes the general characteristics of this approach and compares its performance to laboratory-based commercial kits.

This prior work provided a unique solution to problems relating to low cost biomolecular isolation, separation and detection technology, where reactants are rendered "mobile" by disposing them on particles which can be easily manipulated through various "zones" of an apparatus or system. The different zones separate various solutions, including reaction and processing zones. One important aspect of the disclosure is the use of surface tension valves to segregate the different zones while permitting the transport of the particles through each zone. Surprisingly, the particles can pass through these air valves despite considerable surface tension, and can do so without transferring liquids from one chamber to another. Thus, the present disclosure can solve many problems currently limiting the application of biomolecular isolation, separation and detection technologies and create new areas of application as well.

This present disclosure describes a method to improve the stability of the "surface tension" valves described in the inventors' previous work. The design described here is a simple and inexpensive means to manufacture and store pre-arrayed devices with surface tension valves so that they are much more attractive as a commercial product with a long shelf life. In previous designs, the inventors we described using oil or other liquids as spacers between pre-arrayed solutions of a processing chemistry. Here, they envision substituting wax and wax-like materials for the liquid spacer valve structures. These inert structures will be designed to be stable (i.e., highly viscous or solid) at room temperatures (or any storage temperature), but can easily be melted by applying heat to the tubing in which they are arrayed. As the wax liquefies, it becomes oil-like and remains in place as with the previous designs (typical changes in viscosity show a 1000-fold drop in viscosity over from room temperature to 60 to 90° C.; this change in viscosity is required to permit microbeads to passage through the valve position during processing but prevent microbead passage and adjacent solution mixing at room temperatures), separating neighboring processing solutions. Once in the liquid state, an external magnet is used to pull magnetic beads from one solution to the next to effect processing of structures on the surface of the magnetic beads, just as with the previous studies. These and other aspects of the disclosure are described in greater detail below.

A. The Device

In general, the device will have the following components. First, a continuous tubing will provide the basis for creating a plurality of chambers. The chambers are, in essence, liquid pockets that are maintained separate from each other by the use of surface tension valves, which are fluid or gaseous agents interspersed between the fluid pockets. The device may also include predisposed therein particles for use in detecting analytes that are introduced into the device. Finally, the device may be provided without the liquid pockets, but instead may contain the liquids and fluid/gaseous components in separate containers (i.e., a kit) for use or distribution into/customization of the device at the point of implementation. The individual elements of the device will be discussed in greater detail below.

1. Tubing

Central to the design of this device is the establishment of a series of solutions arrayed along a tube each separated from the next by a surface tension valve. Only tubing of sufficiently small diameter will allow for a stable arrangement of the fluids and valves, as discussed above in the Summary. Tubing of diameter greater than about 4 mm will not support stable valve formation, although diameters somewhat larger are permitted when the valve is only partially opened by heating. Therefore an important physical property of this component is its diameter.

The tubing may be made of a variety of different materials, including glass, polymers or metal. The tubing should be made of, or internally coated with, a polymer that permits formation of surface tension valves, discussed further below. It is also desirable to have tubing with low surface energy, meaning that it is non-binding for proteins, and also hydrophobic. These properties of the tubing material affect the stability of the arrayed solutions and therefore the diameter of the tubing that is useable. Lower surface energy generally will require a tubing of smaller diameter to permit stable valve formation. Typical surface energy values for glass, silanized glass, polystyrene, Teflon and some types of fluorinated ethylene polypropylene Tygon tubing are in the range of 10-50, 10-30, 15-30, 20-30, 5 mN/m, including 10, 15, 18.5, 20, 25, 30, 35, 40, 45 and 50 mN/m.

A particular type of tubing is Tygon tubing, which is a brand name for a variety of flexible tubing. Tygon is a registered trademark of Saint-Gobain Corporation. Tygon tubing is used in many markets including food and beverage, chemical processing, industrial, laboratory, medical, pharmaceutical, and semiconductor processing. There are many formulations of clear, flexible, Tygon tubing. The chemical resistance and physical properties vary among the different formulations, but the tubing generally is considered resistant to almost any chemical attack.

Several formulations of Tygon are Class VI approved and can be used in either surgical procedures or pharmaceutical processing. Medical versions include the following:

Tygon Medical/Surgical Tubing S-50-HL—Characterized to the latest ISO 10993 standards and FDA guidelines for biocompatibility. This material is non-toxic, non-hemolytic, and non-pyrogenic. This formulation is used in minimally invasive devices, dialysis equipment, for bypass procedures, and chemotherapy drug delivery.

Tygon Medical Tubing S-54-HL was introduced in 1964 for use in medical applications. This material can be used in catheters, for intravenous or intra-arterial infusion and other surgical uses. Tygon S-54-HL can also be fabricated into cannulae or protective sheath products using thermoforming and flaring techniques.

Pharmaceutical Tygon includes:

Tygon LFL (Long Flex Life) pump tubing is non-toxic clear tubing with broad chemical resistance. It is often used in product filtration and fermentation and surfactant delivery.

Tygon 2275 High Purity Tubing is a plasticizer-free material that is often used in sterile filling and dispensing systems and diagnostic equipment. This formulation is also considered to have low absorption/adsorption properties, which minimizes the risk of fluid alteration.

Tygon 2275 I.B. High-Purity Pressure Tubing is plasticizer-free and is reinforced with a braid for use with elevated working pressures.

Tygon chemfluor FEP is a non-protein binding tubing that contains no additives or plasticizers. FEP stands for fluorinated ethylene propylene.

Peristaltic applications include the following:

Tygon R-3603 Laboratory Tubing is commonly used in university laboratories. It is often used in incubators, hoods and as a replacement for rubber tubing for Bunsen burners. This material is produced in vacuum sizes and can withstand a full vacuum at room temperature.

Tygon R-1000 Ultra-Soft Tubing is used in general laboratory applications. It is the softest of the Tygon formulations with a durometer hardness of Shore A 40 (ASTM Method D2240-02). Because of the low durometer of this material it is often used in low-torque peristaltic pumps.

Tygon LFL (Long Flex Life) Pump Tubing, Tygon 3350, Tygon S-50-HL Medical/Surgical Tubing, Tygon 2275 High Purity Tubing, and Tygon 2001 Tubing are also used in peristaltic pump applications.

FEP Tubing, or fluorinated ethylene propylene, such as TEXFluor@ FEP tubing, is available in smoothbore, convoluted, corrugated, kink resistant retractable coils and heat shrinkable.

Other types of tubing include the following. Silicone Tubing (LPS), which is the most commonly used peristaltic pump tubing. It provides the longest service life and good chemical compatibility for aqueous solvents. Silicone tubing can be autoclaved a single time using a wet cycle. Vinyl Tubing (LPV) has the lowest per-foot cost of the available peristaltic pump tubing. It generally has only fair compatibility for most aqueous solvents and does not have a good tolerance for organic solvents. It has only about one-third the service live of silicone tubing in a peristaltic pump. Vinyl tubing should not be autoclaved or exposed to temperatures above 80° C. Fluoroelastomer Tubing (LPF) is both the most chemically inert and the shortest lived peristaltic pump tubing. It can even withstand halogenated solvents for a limited time. Its service life is only about one-twentieth that of silicone tubing in a peristaltic pump. Like silicone tubing, fluoroelastomer tubing can be autoclaved a single time using a wet cycle. Teflon® Tubing (HPT) is among most inert of all the tubing manufactured. It can withstand nearly any solvent used in a modern laboratory, from distilled water to methylene chloride. Its excellent thermal characteristics allow it to be autoclaved repeatedly. After autoclaving Teflon tubing should not be used for fluid transport until it has cooled. Polyethylene Tubing (HPP) is an inexpensive alternative to Teflon tubing. Like Teflon tubing, polyethylene can handle pressure significantly higher than any of other flexible tubing. Polyethylene does not have the thermal stability of Teflon so it should not be autoclaved; it can, however, be sterilized using ethylene oxide.

2. Chambers

The present inventors have designed processing chambers, equipped with gas/fluid valves, which permit the passage of particles into and out of the chambers without substantial loss of liquids, and preservation of each compartment's integrity. In a particular embodiment, the processing chambers are configured to provide down to nanoliter volumes. Reaction, processing, hybridization, and analysis steps can be conducted in a series of separate chambers. In general, the chambers contain aqueous liquids that contain various chemical and biological species, such as salts, dyes, labels and other chemical species. Examples of the disposition of the chambers and their relationship to one another are illustrated in FIGS. 1-4.

Figure 8:
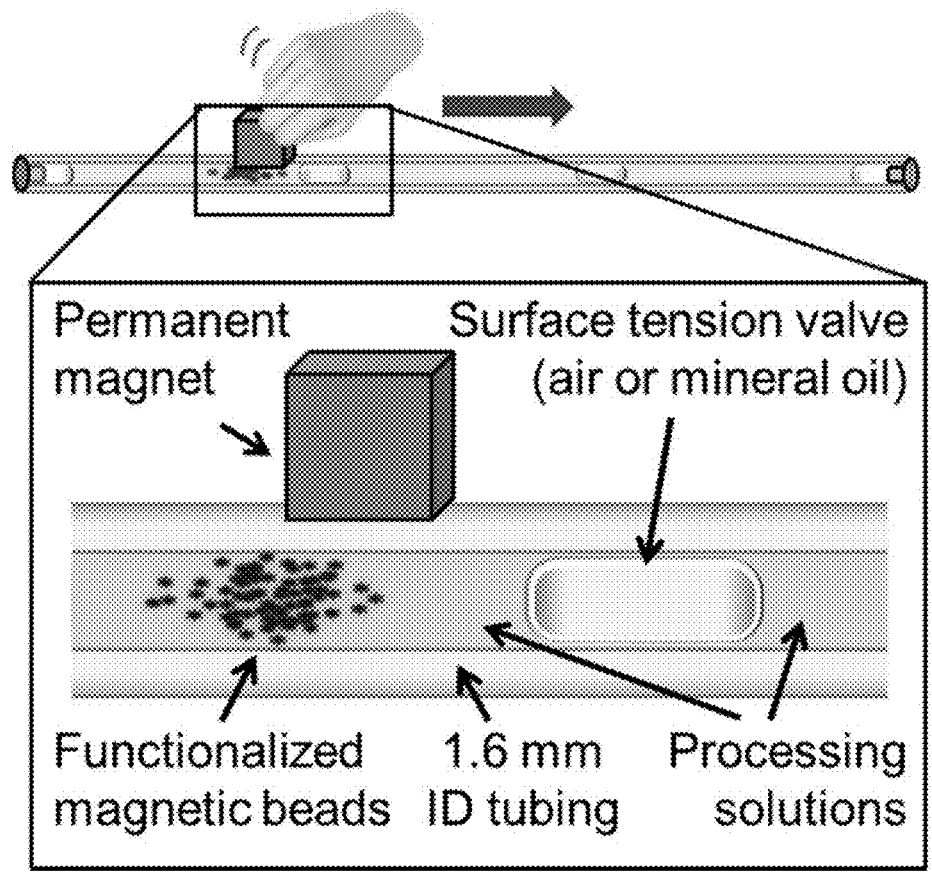
FIG. 8—Design of the prototype extraction method showing three processing solutions held in place in plastic tubing and separated by surface tension valves. Cells are bound to magnetic beads, which are then pulled through a series of washes in a plastic tube using a magnet. The cells are dissociated from the beads following processing.

Referring to FIG. 1, the user is shown pulling a cube magnet along the sections of tubing joined by plastic pipette tips containing air (substituted with wax material here). The motion of the cube magnet transports magnetic particles across the solution/air interfaces. In the inset, the arrow shows the beads entering the air separating the two liquid solutions. Another embodiment is shown in FIG. 8, where air is replaced with a wax-like material and heating is used to change the valve material to one with a lower viscosity.

Figure 2:
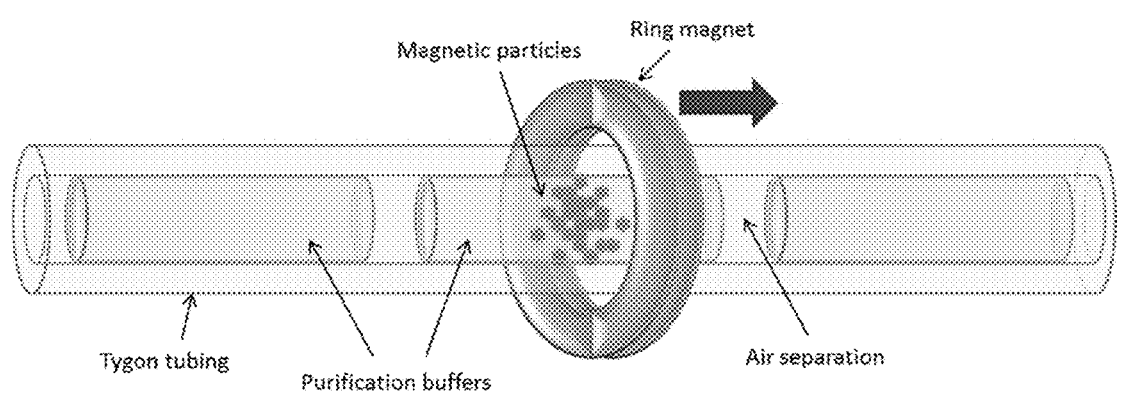
FIG. 2—Magnetic ring device "pull-through" embodiment. Design of the continuous tubing extraction cassette showing individual processing solutions separated by surface tension valves. An external magnet is used to pull whole cells adsorbed to reactant-coated magnetic particles through each processing solution. Following processing, the whole cell is eluted in a final water chamber.

Referring to FIG. 2, a doughnut shaped magnet is manually passed along the tubing and this transports magnetic particles. In the inset, the arrow shows the beads attempting to pass through an air surface tension valve (substituted with wax here).

Figure 3:
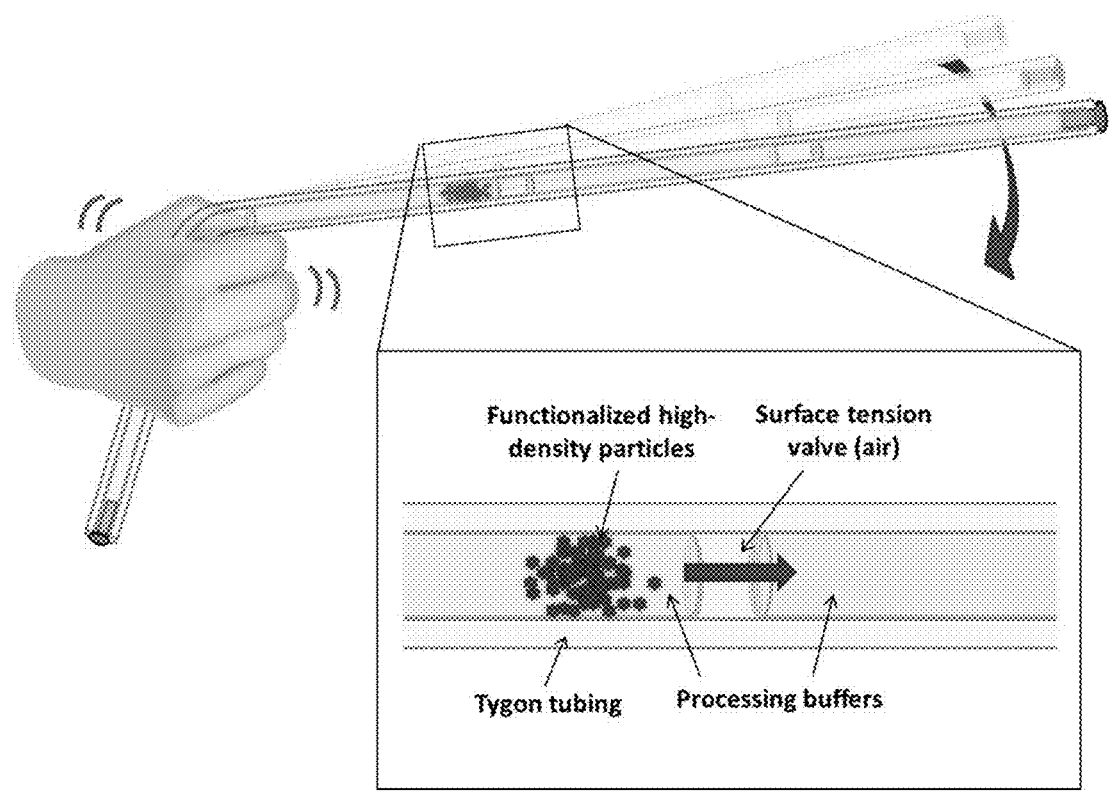
FIG. 3—Low resource processor based on centrifugal force transport of dense beads outward along the extraction cassette.

Referring to FIG. 3, the user is shown driving high density particles down the tubing with hand generated centrifugal force. In the inset, the arrow shows the beads attempting to pass through an air surface tension valve (substituted with wax here).

Figure 4:
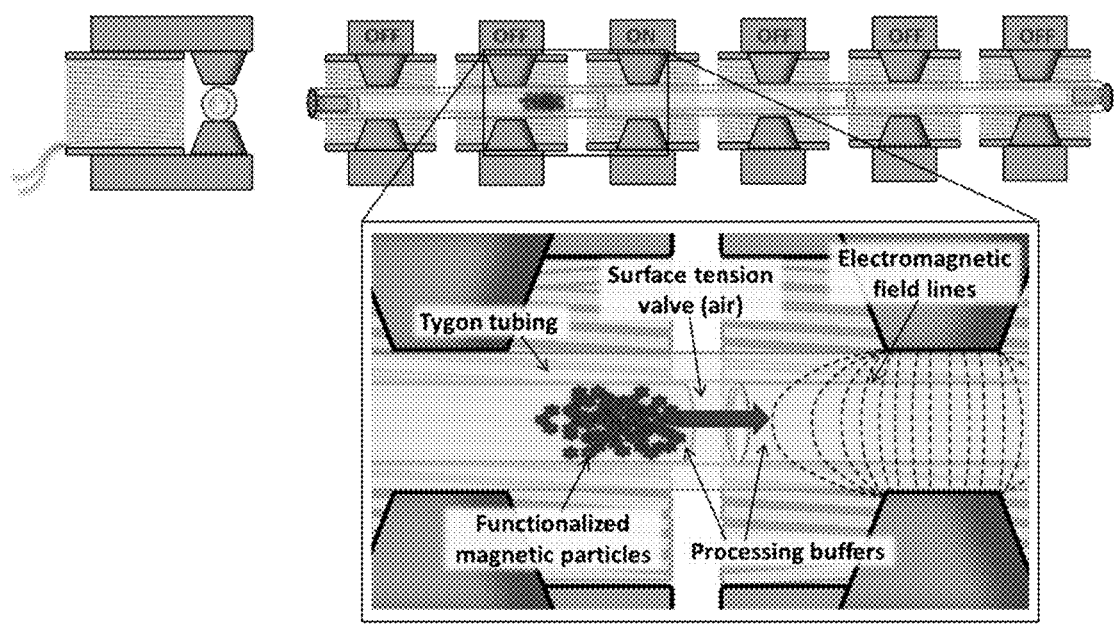
FIG. 4—Automated processor design. Views of an electromagnetic design for transporting magnetic particles from one processing solution to the next. Series of 6 electromagnets arranged in a linear array around a closed tube. Electromagnetics are turned on and off the create transient magnetic fields for pulling the magnet beads across the surface tension interface separating successive processing solutions.

Referring to FIG. 4, a series of c-clamp electromagnets are disposed along the tubing. By subjecting the electromagnets to sequential activation, the magnetic particles are transported along the length of the tubing. In the inset, the arrow shows the beads attempting to pass through a water/air surface tension valve (substituted with wax here).

Figure 12:
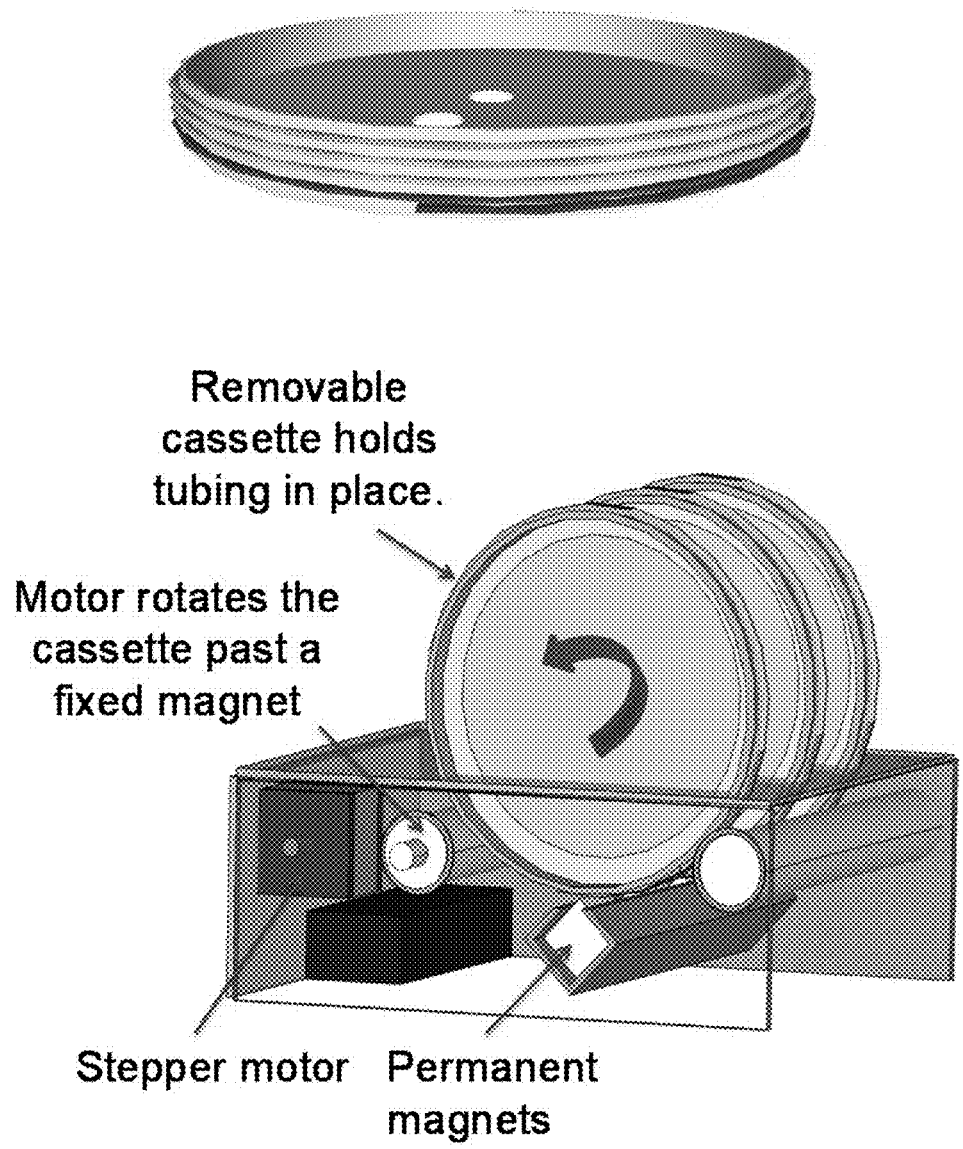
FIG. 12—Example of an automated design based on a fixed magnet and a rotating cassette.
Figure 13:
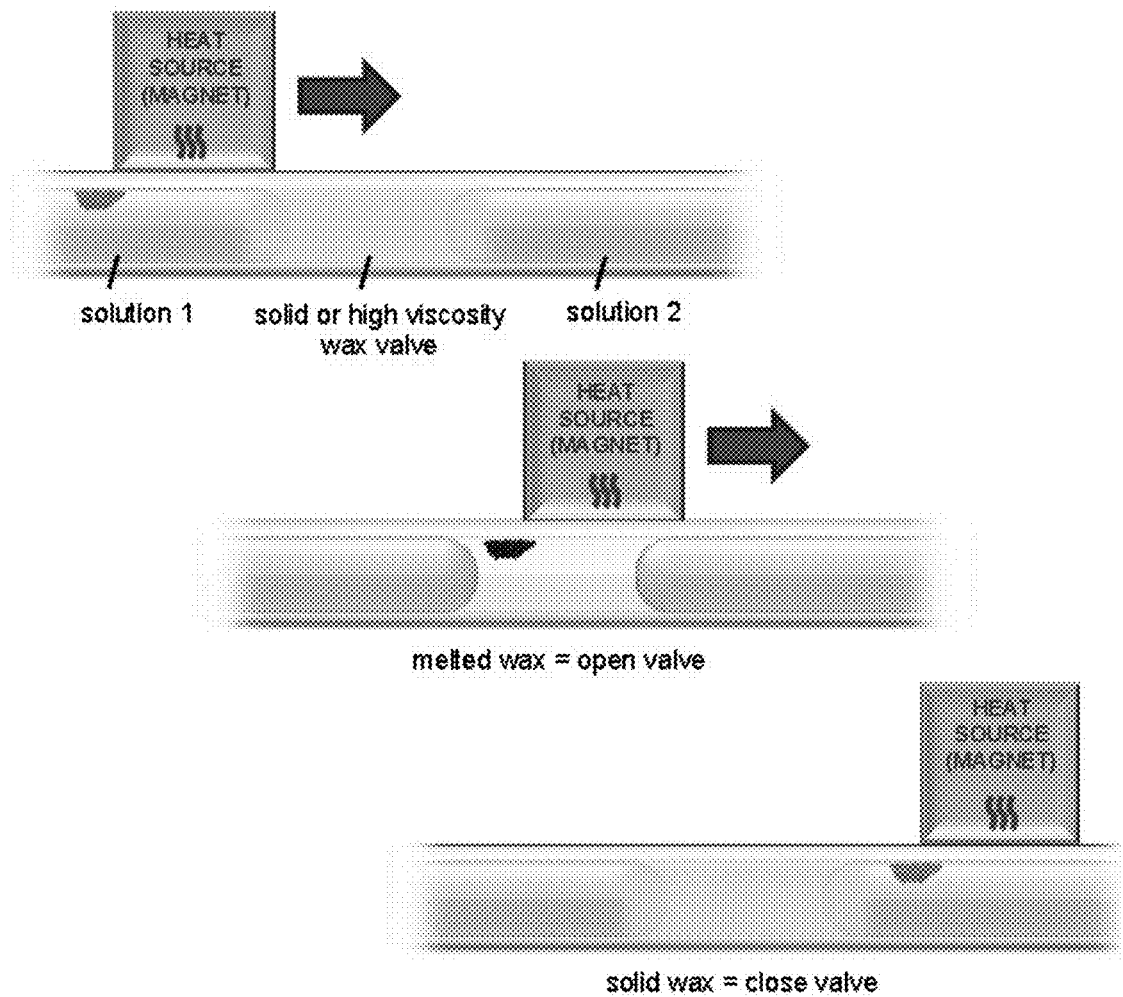
FIG. 13—Illustration of heated magnet embodiment for liquefying plug and transport of bead.

Referring to FIG. 12, an automated device is shown wherein the sample cassette is rotated past a fixed magnet by a motor.

Reaction Chambers.

One type of chamber is a reaction chamber. In a reaction chamber, the cell associates with the reactant on the surface of the particle. Such a reaction chamber would be unnecessary in an embodiment where the particles are mixed with a sample prior to introduction into the device. Generally, a reaction chamber will provide suitable conditions under which the reactant on the particle and the cell may interact.

The reaction chamber may optionally include agents to inhibit non-specific interactions or to stabilize interactions once achieved.

Processing Chambers.

A variety of different types of chambers may be used in accordance with the present disclosure. It also is possible, where convenient, to have a series of processing chambers. A processing chamber may also be reused in the sense that the flow of the particles may be reversed so that a given chamber is used more than once. The present disclosure may also utilize multiple processing chambers where different solutions are included therein.

One example of a processing chamber is a pretreatment chamber. It is often the case that reactants, samples or particles will be "pretreated" in such a way as to ensure that the ensuing reaction with the target has a high degree of fidelity, i.e., minimize non-specific attachment. A classic example of a pretreatment is a "blocking" reaction. Non-specific protein-protein interactions are inhibited by pre-treating a substrate with a non-specific protein, such as BSA. Similarly, non-specific DNA reactions can be reduced by incubating the probe with a "random" DNA known to lack homology with the probe. Another example of a pretreatment is removing a known cross-reactive species. In the case of isolating CD4+ T cells, it may be desirable to first remove CD14+ monocytes, which also express low levels of CD4. In this case, a pretreatment chamber will precede a reaction chamber.

Another important step when assessing the reaction of biomolecules is to remove non-specifically bound molecules from the reactant. Though achieving the same goal as pretreatment, washing takes place after the exposure of reactant to target. Typically, wash solutions comprise a buffer similar to that used in the target solution, but lacking the target itself. Occasionally, it will be desirable to alter the chemical properties of the wash solution by, for example, changing the salt concentration or pH. Wash chambers would follow a reaction chamber.

An additional chamber may be included into which the species of interest is released during the final extraction process. This chamber's function is to provide the elution step of many extraction processes. This chamber may also effectively function as a concentrating chamber since if its volume is sufficiently small compared to the original sample volume, the number of molecular targets will be higher than in the initial sample, thus effectively concentrating this species.

In some embodiments, it may be desirable to recursively amplify signals relating to binding of target cells to reactants, or to generate more targets for reaction. There are a variety of mechanisms for accomplishing this. However, a common feature will be the need for one or more chambers, prior to or following a reaction chamber, which effect the necessary steps to achieve the amplification.

Finally, in order to increase the efficiency of the process, particles may be retrieved from downstream processing chambers and be returned to an upstream reaction or processing chamber, either by extraction and reintroduction or by reversal of the transport mechanism (e.g., centrifugal force, density or magnetic). By repeating the reaction and/or processing steps, one can increase both the signal and specificity of binding and detection.

Figure 5:
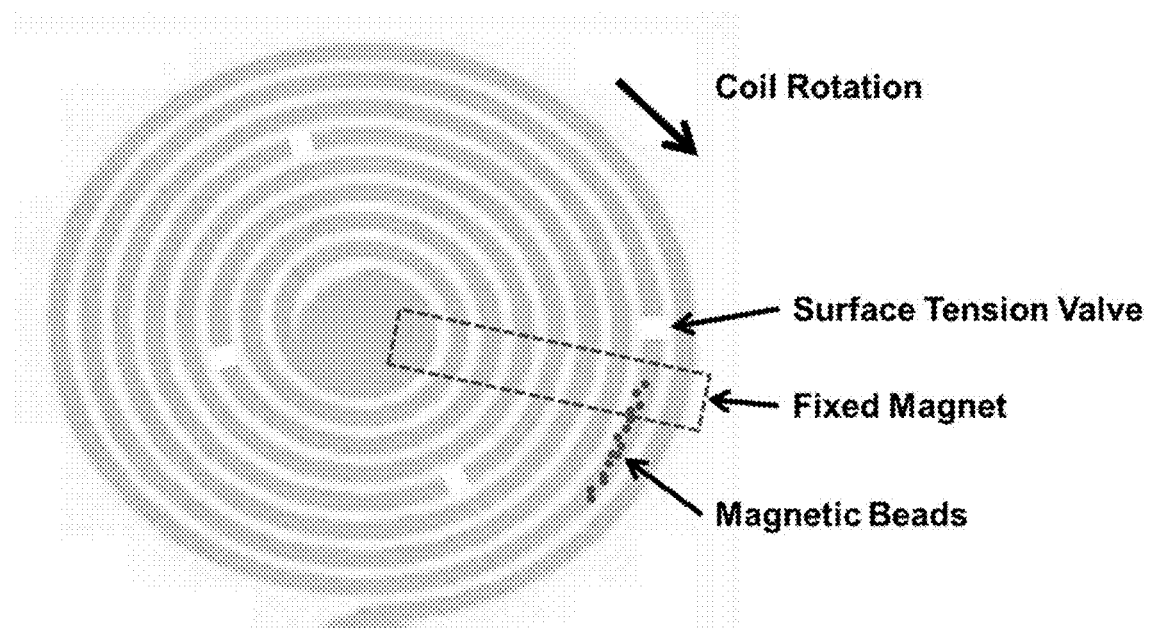
FIG. 5—Automated processor design. Top view of a coiled processor design. Fluid filled tubing contains four surface tension valves separating the five processing solutions. The coil is rotated under a fixed magnet and the magnetic beads are moved by the magnetic field through a series of processing solutions.

Thus, FIGS. 1-4 and 8 show embodiments of chambers arrayed in linear array. Tubing may also be flexible and as shown in FIG. 5 an additional embodiment may be a flat coiled design that shows the tubing arrayed a coil that slowly rotates to pull the magnetic particles from one chamber to the next.

3. Surface Tension Valves/Plugs

An important aspect of the disclosure is the use of surface tension valves to separate the tubing into discrete chambers. These surface tension valves allow flexibility in the composition of the processing fluids and the movable substrate.

In essence, the surface tension valve is simply a nonreactive gas or liquid that separates various sections of the device by creating a stable interface with the fluids that make up the various chambers. Important aspects of the gas or liquid include low vapor pressure or low surface tension, which are defined as having a vapor pressure significantly less than 1 kPa and a surface tension between 2 and 100 mN/m, including about 72 for air/water, about 50 for water/mineral oil, and about 3.3 for benzyl alcohol/water (values are from Handbook of Organic Solvents) (Lide, 1995) (incorporated by reference). Liquids include Mineral oil, Dodecane, 1-Dodecene, Tridecane, Methyloleate, Acetophenone, Propyl Benzoate, or 1-Methylnaphthalene. Also, addition of certain materials can alter the surface tension interface, e.g., Tween® can lower the surface tension.

Of particular relevance to the present disclosure is the use of solid "plugs" to replace the liquid surface tension valves prior to use. The advantage with this design is that the plugs are far more stable during storage and transportation. The requirements for the plug material are that (a) they are solid or highly viscous at normal storage and transportation temperature (e.g., somewhat below normal room temperature up to about 45° C.), but upon being subject to higher temperatures (e.g., 45-60° C. or higher, depending on the format), they become liquid and retain the appropriate characteristics of surface tension valves, as defined above.

A variety of commercially available long chain hydrocarbons (C24 or greater) can be employed to create the plug materials. The plugs can be engineered with melting temperatures from at or about the 45° C. or ° C. level in escalating 2-3° C. increments up to the maximum values contemplated (about 80° C. to about 95° C.). In some situations, it may be advisable to have multiple plugs in the same device with differing melting temperatures, particularly in cases where the entire device is subjected to a heat source at the same time. Alternatively, the plugs may be of the same material and/or melt at the same temperature.

In general, melting temperatures of the plug material will exceed 45° C. or great, 50° C. or greater, about 60° C. or greater, about 65° C. or greater, about 70° C. or greater, about 75° C. or greater, about 80° C. or greater, about 85° C. or greater, about 90° C. or greater, or about 95° C. or greater. Ranges of melting temperatures for the plug materials include about 45° C. to about 50° C., about 45° C. to about 60° C., 60° C. to about 95° C., about 60° C. to about 80° C., or about 60° C. to about 70° C.

There are specialized applications where lower melting temperatures might be used. For example, if heating in excess of 50° C. causes mRNA dissociate from oligo dT beads, a wax (or oil) with a melting temperature in a range that would retain the mRNA on the surface (e.g., between about 40° C. and 60° C.), such as coconut oil, could be used.

In a particular embodiment, the plug will contain materials that, upon heating and liquefaction, return to a solid state that is far more heat-resistant than the original plug, i.e., cannot be melted at the original melting temperature and may have a melting temperature that is much higher that can easily be applied—essentially being rendered a permanently solid plug. This embodiment might entail use of a two-part epoxy where the materials are kept separate by the plug material and become mixed upon heat and liquefaction of the normal plug material. The epoxy materials (e.g., resins) then react and form a heat stable permanent plug.

There a number of ways that transport of the particles across the surface tension valve can be achieved as illustrated in FIGS. 1-5 and 8. For example, an external permanent magnet, an external movable electromagnet, centripetal force applied by tube motion around one end, and density driven (i.e., a heavy particle falling under gravity or a buoyant particle moving upward in less dense fluid).

4. Particles

The particles for use in the present disclosure combines the functionalities of preferential binding to a class of molecules or to a select target of interest, susceptible to transport by external force (e.g., magnet, or density differences), and small size to increase reaction efficiencies.

The particles may be synthesized using a variety of materials, such as metal, ceramic, glass, or a polymer. In particular, the particles are magnetic or paramagnetic for embodiments where magnetic fields are employed. In embodiments where centrifugal force is applied, the particles should have a density of >1.

Commercially available particles include those provided by SIGMA-ALDRICH and include polystyrene, polystyrene monodisperse, magnetic, melamine resin, melamine resin-carboxylate modified, polymethacrylate and silica (including beads coated with any of the foregoing substances).

Figure 6:
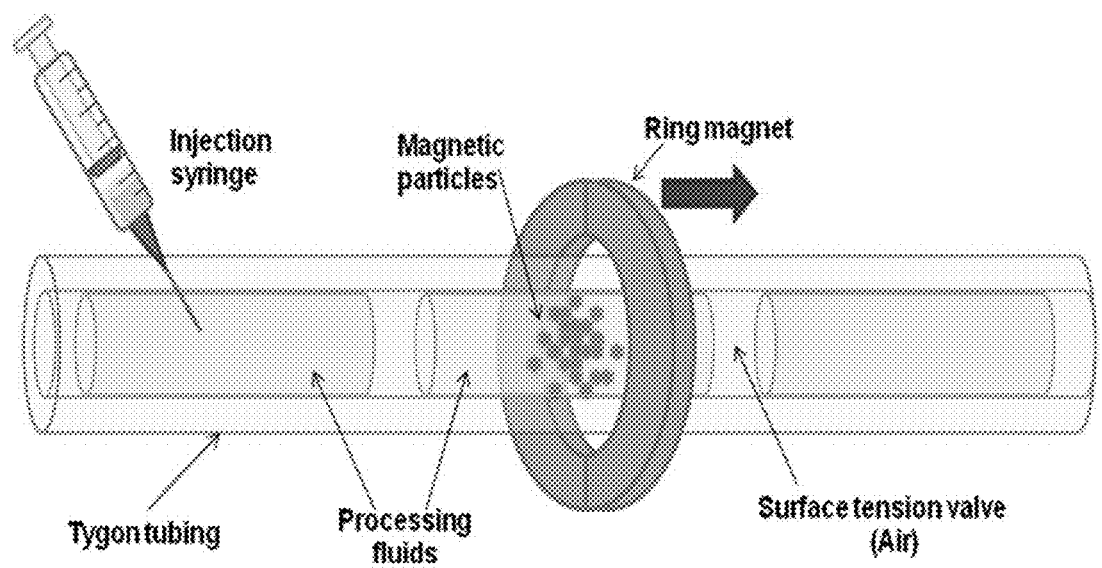
FIG. 6—Low resource point-of-care extraction processor illustrating the use of surface tension valves (in this case liquid/air interfaces; substituted with solid or semi-solid plug material here) to separate liquid processing steps. A biological sample is injected into the left chamber (syringe) followed by movement of reactant-coated magnetic beads from this chamber into the second using an external ring magnet. In this illustration, the captured material is released in the final chamber on the right.
Figure 7:
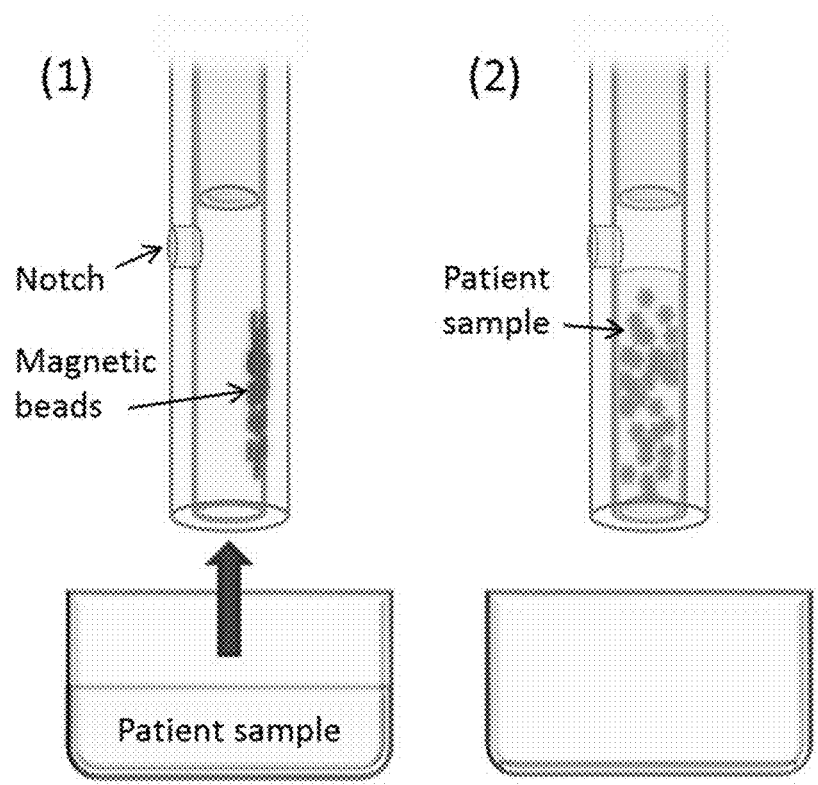
FIG. 7—Extraction cassette loading design. Method of introducing a patient sample into one end of an extraction cassette. (1) The end of the cassette is lowered into the patient sample and capillary action draws the patient sample up into one end of the cassette (2), where it interacts with magnetic beads dried on the inner surface of the tube. An external magnet is then used to transport the beads through the surface tension valves and processing solutions contained in the upper section of the tubing.

Introduction of the particles/sample into the cassette may be achieved in a number of methods. FIG. 6 illustrates injection of a sample through the wall of Tygon tubing. Particles may be mixed with the sample before injection or particles may be already present either in suspension or dried within the first section of tubing. FIG. 7 illustrates a second embodiment for loading particles/sample through capillary action. In this embodiment, capillary forces present in small diameter tubes result in the drawing up of the sample into the first section of the cassette. Particles may be mixed with the sample before being drawn up or dried along the first section of tubing in which case they are released when they come into contact with the advancing fluid. Transport of particles among the following chambers proceeds as described above.

5. Kits

According to the present disclosure, there are provided kits containing the devices described above. Generally, kits comprise separate vials or containers for the various reagents, such as particles, reactants, and detection reagents—either as liquids or as lyophilized solids. In the case of the latter, suitable solvent may be included, such as water, ethanol, various buffer solutions, and the like. The reagents may also be provided in the device in a ready-to-use form, i.e., with chambers and surface tension valves already established in the device. The device, particles, reactants and/or reagents may be disposed in vials or containers held in blow-molded or injection-molded plastics, or in tubing coiled within a flat circular cassette.

6. Heating

Heating of the device will be required in order induce a substantial reduction in viscosity of the plug material sufficient to permit movement of beads through the resulting surface tension valve prior to or during use. The plug material may return to a solid state upon withdrawal of the heat source. Melting can be performed prior to any other step, at the time of sample introduction, or during sample processing and/or movement. The heating should be conducted at a temperature that does not damage the sample or any of the reactants in the device, or the device itself. It should also not interfere with any of the reactions taking place within the device (e.g., binding, enzymatic activity, detection).

Heating may involve heating the entire device or portions thereof, in particular, the plug material or portions of the device adjacent thereto. Heating may involve using heated forced air (e.g., a hair dryer), a radiant heat source placed adjacent to the plug material, or simply placing the device or portion thereof in an environment with a temperature sufficient to melt the plug material (e.g., an oven; or a microwave, where plug contains embedded metal (e.g., gold) particles that, when irradiated externally, heat the plug more quickly than other portions of the device). A particular embodiment involves heating a magnet, or material attached to or placed next to a magnet, and moving the heated magnet/material over the region of the plug material, effecting melting.

The heating may result in the entire plug material being melted, or it may result in melting of only a portion of the plug material, such as the periphery of a cylindrical plug, or one side of a plug. Following melting, the resulting surface tension valve may remain in liquid state for the duration of the use of the device, or it may revert to solid form after the sample has passed through the surface tension valve.

Heating may take place at a fixed temperature, or over a temperature range, such as where multiple plug materials are present and melt at different temperatures. In general, melting temperatures will exceed about 45° C., more particularly about 50° C., and more particular be about 60° C. or greater, about 65° C. or greater, about 70° C. or greater, about 75° C. or greater, about 80° C. or greater, about 85° C. or greater, about 90° C. or greater, or about 95° C. or greater. Ranges of melting temperatures include about 45° C. to about 60° C., about 45° C. to about 90° C., about 60° C. to about 95° C., about 60° C. to about 80° C., or about 60° C. to about 70° C. Somewhat higher temperatures (95° C. to 120° C.) may prove useful for industrial applications.

B. Reactants and Targets

Another important aspect of the disclosure is the reactants that are disposed on the surface of the particles, and the targets with which these reactants interact. By reactant, it is not necessary that the material interact in any particular type of way. Rather, any physical interaction that permits association of reactant with the target cell is envisioned, such as covalent, non-covalent, electrostatic, hydrostatic, or ionic. For example, by coating a particle with an antibody, one can absorb cells expressing the antigen for said antibody to the particle to the exclusion of other biomolecules. Molecules that coordinate metals, in particular heavy metals, are also envisioned as reactants. Nickel and cobalt are in particular contemplated. One can also use non-specific binding to pull out a more general class of compounds based simply on their relative interaction with the reactants.

The analyte may be whole cells of any type, or a cell component. The reactants can be any of a wide variety of biomolecules including proteins or nucleic acid aptamers. Other reactants include amino acids and small organic molecules. For two nucleic acids, the binding interaction will generally be characterized by hybridization, achieved by homologous base pairing. For one or more protein molecules, the interaction will generally be the formation of protein-ligand complexes which are reliant on the complementary structure and charge of the component molecules, such as antibody-antigen interactions and receptor-ligand interactions. Various types of molecules suitable for use in accordance with the present disclosure are described below.

Nucleic acids, proteins, small molecules, and other targets may be detected as described below as a means of detecting an isolated whole cell. They may also be detected apart from a whole cell, for example, as a second analyte for multiplex detection.

1. Cells

Whole cells may be of any origin, including protists, animals, or plants. The cells may be living or fixed at the time of processing. Protists may be of the genus *Plasmodium, Babesia, Leishmania, Giardia,* or *Trypanosoma*. Animal cells may be mammalian, preferably human. Cells may be CD4+ T cells, virus-infected cells, parasite-infected cells, cancer cells, or blood cells. Cells may be processed from whole blood specimens. The whole blood specimen may be fresh.

The cells in the sample may be quantified using a known ratiometric particle for determining cell counts. Absolute cell counts and ratiometric cell counts may be determined using a spectrophotometer.

2. Nucleic Acids

The term "nucleic acid" is well known in the art. A "nucleic acid" as used herein will generally refer to a molecule of DNA, RNA or a derivative or analog thereof, including synthetic molecules. Nucleic acids are also defined as molecules containing a series of naturally-occurring purine or pyrimidine bases. The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to both single-stranded and double-stranded molecules, the latter being substantially or fully complementary to each other. A nucleic acid may even encompass a triple-stranded molecule. As used herein, a single stranded nucleic acid may be denoted by the prefix "ss," a double-stranded nucleic acid by the prefix "ds," and a triple stranded nucleic acid by the prefix "ts."

(b) DNA

DNAs are defined as nucleic acids containing adenine "A," guanine "G," thymine "T" and cytosine "C." DNA molecules, both single- and double-stranded, may be utilized in accordance with the present disclosure. DNAs may comprise coding sequences or non-coding sequence, and genomic sequences or cDNAs, synthesized strands homologous to the target of interest. DNA "arrays"—collections of DNAs that represent a group of selected probes.

(c) RNA

RNAs are defined as nucleic acids containing A, G, uracil "U" or C. Both single- and double-stranded RNAs, may be utilized in accordance with the present disclosure. Because of their labile nature, additional steps must be taken to preserve the integrity of RNA containing samples. In particular, the ubiquitous presence of RNAses requires the use of RNAse inhibitors such as DEPC.

3. Proteins

In another embodiment, the probe may be a proteinaceous compound. There are wide varieties of protein-protein interactions; however, proteins also bind nucleic acids, metals and other non-proteinaceous compounds (e.g., lipids, hormones, transmitters). Some examples of protein that may be used as either targets or probes are listed below.

(a) Antibodies

Antibodies may be used as probes for unknown molecules, or they maybe the target for reaction with a known probe. The antibodies may be either polyclonal or monoclonal in origin. Method for preparing antibodies are well known to those of skill in the art and need not be discussed here. Antibodies may be fixed to the filament support using standard techniques.

Obviously, identifying antibodies that bind to certain target molecules is an important goal that could be accomplished by the present disclosure. However, the present disclosure also permits the screening of samples for the presence of antibodies. For example, a particle might contain a variety of bacterial and viral antigens, which could assist in diagnosis of infectious disease by identifying relevant antibodies in an affected subject.

(b) Enzymes

Enzymes are proteins that facilitate the modification of a wide variety of compounds including nucleic acids, other proteins, lipids, sugars, steroids and many other compounds. Particular types of assays contemplated include identifying inhibitors of enzymes that bind to, but are not processed by, the enzyme. Alternatively, identifying compounds that are bound by an enzyme may assist in design of pro-drugs that are processed by an enzyme.

(c) Receptors

Receptors are molecules that facilitate signaling processes by binding their cognate ligand moieties. Once bound, the receptor will then perform some other function (enzymatic, intracellular translocation, cell permeability) that effects the signaling. Identifying molecules that block receptor function, or mimic the natural ligand, can be accomplished using the present disclosure.

(d) DNA-Binding Proteins

Another important class of proteins is the DNA binding proteins. These proteins include polymerases, helicases, ligases, and transcription factors. The proteins have varying degrees of DNA sequence specificity can be assessed for ability to bind varying DNA sequences. Conversely, providing a DNA sequence as a probe, once can identify unknown binding proteins with specificity for that sequence.

4. Small Molecules and Other Targets

A wide variety of "small molecules" can be examined for their ability to interact to a given reactant. These libraries comprise non-protein and non-nucleic acid molecules. Alternatively, libraries can be constructed around particular "pharmacores" that are believed to provide basic structural features necessary for a particular drug to function.

Also, compounds such as liquids, carbohydrates, metals, and toxins may be assayed using the devices and methods of the present disclosure.

5. Labels

In various embodiments, it may desirable to label particles, reactant, or target molecules. Examples of labels include paramagnetic ions, radioactive isotopes, chemiluminescent compounds, fluorophores, chromophores, NMR-detectable substances, and X-ray imaging compounds.

Paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

Radioactive isotopes include astatine$^{211}$, $^{14}$carbon, $^{51}$chromium, $^{36}$chlorine, $^{57}$cobalt, $^{58}$cobalt, copper$^{67}$, $^{152}$Eu, gallium[67], [3]hydrogen, iodine[123], iodine[125], iodine[131], indium[111], [59]iron, [32]phosphorus, rhenium[186], rhenium[188], [75]selenium, [35]sulphur, technicium[99m] and/or yttrium[90]. [125]I is often preferred for use in certain embodiments, and technicium[99m] and/or indium[111] are also often preferred due to their low energy and suitability for long range detection.

Among the fluorescent labels contemplated for use include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Enzymes (an enzyme tag) that will generate a colored product upon contact with a chromogenic substrate may also be used. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

C. Definitions

The term plurality, as used herein, is defined as two or more than two.

The term another, as used herein, is defined as at least a second or more.

The terms including and/or having, as used herein, are defined as comprising (i.e., open language).

The term coupled, as used herein, is defined as connected, although not necessarily directly.

The term approximately, as used herein, is defined as at least close to a given value (e.g., preferably within 10% of, more preferably within 1% of, and most preferably within 0.1% of).

The term substantially, as used herein, is defined as at least approaching a given state (e.g., preferably within 10% of, more preferably within 1% of, and most preferably within 0.1% of).

The phrase "any integer derivable therein," as used herein, is defined as an integer between the corresponding numbers recited in the specification, and the phrase any range derivable therein is defined as any range within such corresponding numbers.

D. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—RSV RNA Extraction

One embodiment involves extracting viral RNA from pediatric nasal wash samples. Lysed nasal wash sample is injected through the wall of the Tygon tubing into the first chamber on the left and mixed with silica-coated magnetic particles in guanidine salt buffer present in this chamber. Sample RNA binds to the silica surface. Pre-loaded processing solutions are held in place by the surface tension forces of the valves. Magnetic beads are entrained by an external magnet and pulled through each of the processing solutions. Surprisingly when the beads reach the liquid-air interface they pass through it without entraining solution. Entry into the next solution proceeds similarly until the entire cloud of particles passes through all of the process steps. Processing removes sample contaminants, and RNA is concentrated in 50 µl of water in the final chamber and used in downstream RT-PCR processing to detect the presence of respiratory syncytial virus (RSV). FIG. 8 shows a comparison of RSV RNA extraction using the magnetic pull-through design and several commercial kits.

RNA Extraction from TE Buffer and HEp-2 Cell Lysates Using Continuous Tubing Extraction Cassette.

In another design, 8 processing solutions were preloaded within ~61 cm length of Tygon tubing (1.6 mm i.d.). These solutions were chaotropic wash buffer (300 µL of 4 M guanidine hydrochloride, 25 mM sodium citrate, pH 7.0), two sections containing RNA precipitation buffer (300 µL of 80% ethanol, 5 mM potassium phosphate, pH 8.5), three sections containing a water wash (100 µL of molecular grade water), and RNA elution (50 µL of molecular grade water). The 50 µL elution volume was chosen so that the RT-PCR input would be comparable to other extraction methods such as the Rneasy kit. Each solution was separated from the next by an air gap ~2 mm in length. Three types of extraction test samples were prepared: 5 µL of RSV N gene standard RNA in TE buffer at a concentration of $1 \times 10^6$ copies/µL, 20 µL of Hep-2 cell lysates ($2 \times 10^3$ cells/µL) spiked with 5 µL of RNA standard, or 20 µL of RSV infected Hep-2 cell lysates. Cell lysate samples were homogenized by passage through a 25 gauge needle five times. Prior to extraction, samples were added to 230 µL of RNA-silica binding buffer (230 µL of 2 M guanidine thiocyanate, 25 mM sodium citrate, pH 7.0, 50% ethanol) and 20 µL of silica-coated 1 µm diameter magnetic particles ($3 \times 10^6$ particles/µL) (Bioneer Inc., Alameda, Calif.) and placed on a rotating mixer for 5 minutes at room temperature. After mixing, each sample was loaded into the tubing, and the tubing ends were capped. The particles were collected in the first chamber by the external magnet and pulled through the surface tension valves and each successive chamber at ~4 mm/second using ~5 cm diameter neodymium ring magnet (Emovendo LLC, Petersburg, W. Va.). Particles were dispersed in the chaotropic wash and RNA precipitation solutions by rapidly moving the magnet back and forth before being recollected. In the water wash solutions, the particles were moved at ~8 mm/second to minimize RNA loss by elution during the wash. Finally, the particles were dispersed in the final elution chamber and incubated at room temperature for 5 minutes before removal. Although it was utilized in the prototype design, the elution of RNA at 65° C. was not performed in this final design because it would be impractical in most low resource settings. The final chamber contents were collected for RT-PCR analysis. Each RNA extraction was completed in ~15 minutes.

Example 2—Transrenal DNA Extraction

In this example, four processing solutions were preloaded within ~45 cm length of Tygon tubing having an inner diameter of 1.6 mm. These solutions were chaotropic wash buffer (300 μL, of 4 M guanidine hydrochloride, 25 mM sodium citrate, pH 7.0), two sections containing DNA precipitation buffer (300 μL of 80% ethanol, 5 mM potassium phosphate, pH 8.5), and DNA elution (50 μL of molecular grade water). These solutions were separated from one another by an air gap ~2 mm in length.

A 140 base DNA sequence from the IS6110 sequence of *Mycobacterium tuberculosis* was synthesized by Integrated DNA Technologies (Coralville, Iowa), and $5 \times 10^7$ copies were spiked into 200 μL of synthetic urine composed of (in g/L) 0.65 calcium chloride 31ppendorf, 0.65 magnesium chloride, 4.6 sodium chloride, 2.3 sodium sulfate, 0.65 sodium citrate dehydrate, 2.8 potassium phosphate dibasic, 1.6 potassium chloride, 1.0 ammonium chloride, 25 urea, and 1.1 creatinine (Miro-Casas et al., 2001). The DNA-spiked synthetic urine samples were mixed with 200 μL of DNA-silica binding buffer (4 M guanidine thiocyanate, 25 mM sodium citrate, pH 7.0) and 20 μL (0.8 mg) of Invitrogen Dynabeads MYONE silane beads (Carlsbad, Calif.) and vortexed for 5 minutes at room temperature. After mixing, the sample was loaded into the tubing, and the tubing ends were capped. The particles were collected in the first chamber by the external magnet and pulled through the air valves and each successive chamber at ~4 mm/second using ~5 cm diameter neodymium ring magnet (Emovendo LLC, Petersburg, W. Va.). Particles were dispersed in the chaotropic wash and DNA precipitation solutions by rapidly moving the magnet back and forth before being recollected. Finally, the particles were fully dispersed in the DNA elution chamber and removed, and the final chamber contents were collected for PCR analysis. Each DNA extraction was completed in ~9 min. The extraction efficiency was compared to DNA extracted using the Qiagen Dneasy kit according to manufacturer's instructions.

A 129 base fragment of the IS6110 sequence was amplified using forward primer 5'-ACCAGCACCTAACCGGCT-GTGG-3' (SEQ ID NO:1) and reverse primer 5'-CATCGTG-GAAGCGACCCGCCAG-3' (SEQ ID NO:2) (Cannas et al., 2008). Reactions were performed in a 25 μL volume using 5 μL of DNA template and the Qiagen Quantitect SYBR green PCR kit according to manufacturer's instructions. Thermal cycling consisted of 94° C. for 15 minutes to activate DNA polymerase, and 40 cycles of 94° C. for 15 s, 62° C. for 30 s, and 72° C. for 30 s using a Rotor-Gene Q thermal cycler (Qiagen, Germantown, Md.). Product specificity was confirmed using melting curve analysis. Data was collected and $C_t$ values recorded by Rotor-Gene Q Software (Qiagen, Germantown, Md.) and converted to number of copies of DNA per μL using a standard curve.

Example 3—Protein Isolation Using Air/Liquid Interface

DNA extracted from spiked synthetic urine was recovered at an efficiency of 27.15±1.10%. This corresponded to a DNA elution concentration of 271,500±11,020 copies/μL. DNA extracted using the DNEasy kit was recovered with an efficiency of 68.6±3.48%. The corresponding DNA elution concentration was 686,000±34,780 copies/μL. Recovery efficiency was calculated by dividing the total number of extracted copies by the initial number of copies present in the sample and multiplying by 100%.

With a strip of Tygon® tubing cut to 9.5" in length, laid horizontally on the benchtop, insert 10 μL of Buffer B (50 mM sodium phosphate pH 8.0, 300 mM NaCl, 500 mM imidazole, 0.05% Tween-20) into the right end of the tubing using a gel tip pipette tip and seal that end with the rounded end of the MelTemp capillary tube (only insert the glass ⅛" into the Tygon® tubing). Fill a 1 mL syringe with Buffer A (50 mM sodium phosphate pH 8.0, 300 mM NaCl, 200 mM imidazole, 0.05% Tween-20). Carefully remove all air bubbles from the syringe cylinder and needle and dispense buffer until black syringe cap rests at the 1 mL tick mark. ⅛" from the left side of the elution chamber insert the syringe needle into the wall of the tubing and dispense 0.1 mL of Buffer A. ⅛" from the left side of the above wash chamber, insert the syringe again into the wall of the tubing and dispense 0.1 mL of Buffer A. Repeat a third time to yield 3 wash chambers. Insert the cut end of a PCR tube (that has been cut at the rounded end to have a small circular opening) into the right hand side of the tubing, making sure the Tygon® tubing completely seals around the bottom of the tube and there are no puckers or creases in the PCR tube. Using a syringe needle, puncture a small hole into the cap of the tube to serve as a release valve.

Holding the extraction tubing upright, pipette 100 μL of sample into the PCR tube followed by 100 μL of Buffer C. Ensure proper mixing of the sample to fully lyse all cells. To the loading chamber containing the lysed sample, add 10 μL of 100× diluted Dynabeads® to the PCR tube. Close the cap and seal the hole with a small piece of tape. Lay the tubing on the rotisserie (affix to rotisserie using tape if necessary) and allow the tubing to rotate for 10 minutes in order to properly mix the sample. After 10 minutes, remove the tube from the rotisserie. Collect the beads into a pellet at the cut end of the PCR tube using the donut magnet. Pull the beads through the first air valve and into the first wash chamber. Disperse the beads for one minute using a "back and forth" motion along the length of the chamber. Collect the pellet of beads at the end of the first wash chamber, and then pull the pellet through the air valve and into the second wash chamber. In a similar fashion, pull the beads through the second and third wash chambers, ensuring that the beads are sufficiently dispersed throughout the chamber. Collect the pellet of beads in the third wash chamber, pull the pellet into the elution chamber and disperse the beads using a "back and forth" motion for 10 minutes. After 10 minutes, pull the beads back into the air chamber on the left side of the elution chamber. Using a pipette, remove the 200 μL sample from the sample loading chamber and place into a new Eppendorf® tube. Slice the air valve to the left of the elution chamber in between the bead pellet and the elution chamber with the razor. Place the sliced end of the extraction tubing into an Eppendorf® tube with the MelTemp capillary tube pointing upward. Remove the MelTemp tube and pipette 90 μL of Buffer B into the Tygon® tubing containing the elution chamber in order to flush the chamber into a fresh Eppendorf® tube. Reserve the samples for later analysis. The malaria protein target (histidine rich protein) was extracted from phosphate buffered saline and plasma at efficiencies of approximately 55% and 25%, respectively.

Example 4—Protein Isolation Using Mineral Oil/Water Surface Tension Valve

A device according to the present invention is used to isolate a surrogate target relevant to malaria (HRP-II labeled with the fluorescent compound TAMRA). Amine-terminated magnetic beads (silanized iron oxide, 12 μmol amines/mL, p=2.5 g/mL, 1-4 μm diameter, 25-35 EMU/g) were cross-linked with lysine modified NTA using $BS^3$ as the cross-linker. After crosslinking, the particles were charged with Ni(II) using $NiCl_2$.

For the device, each chamber contains 100 μL of solvent. Between each chamber is ~25-50 μL of light mineral oil as the valve. Tygon tubing of 1/16 in (diameter) is utilized. The chamber content and reactions are as follows:

Chamber 1 (Sample): Sample reacted with Ni(II)NTA magnetic beads

Chamber 2 (Wash 1): 0.1 M phosphate buffer (pH 8.0), 300 mM NaCl, 0.25% Tween 20

Chamber 3 (Wash 2): 0.1 M phosphate buffer (pH 8.0), 300 mM NaCl, 0.25% Tween 20

Chamber 4 (Elution): 0.1 M phosphate buffer (pH 8.0), 300 mM NaCl, 0.25% Tween 20, 200 mM imidazole Chamber 5 (Post-Elution): 0.1 M phosphate buffer (pH 8.0), 300 mM NaCl, 0.25% Tween 20, 200 mM imidazole The device was pre-loaded with chambers 2-5, divided with light mineral oil. Air pockets were avoided as much as possible. Both the target (TAMRA HRP-II, 10 μM binding sites) and BSA (fluorescein BSA, 100 μg/mL) were incubated with Ni(NTA) magnetic beads (100 μM Ni(II)NTA's) for 10 min (100 μL total volume). After incubation, the mixture was injected into the first chamber. A donut magnet was then used to transfer the magnetic beads through the tube. When the beads arrived into a chamber, they were spread out throughout the chamber by quickly moving the magnet back and forth. Next, the magnet was slowly moved across the chamber, oscillating perpendicular to the tube to ensure efficient mixing. This process takes ~1 min. The beads are then collected by the magnet and transferred to subsequent chambers. When the extraction is complete, the chambers were collected and analyzed using fluorescence. The same procedure is applied to a device having a starting chamber comprising BNT-II (1 μM), BSA (40 mg/mL), 100 μM Ni(II)NTA magnetic beads.

Example 5—Extraction of CD4+ T Cells

Single-cell suspensions were prepared from PBMC. Three sets of three samples were prepared: unseparated cells, cell subjected to separation using a protocol modified from Invitrogen's Dynabeads human CD4 T cell isolation product, and cells subjected to separation using the extraction cassette. The isolation efficiency and purity were determined for each sample preparation (FIG. 10). The low yield and purity compared to unseparated cells was likely due to the use of insufficient quantities of separation beads for a very concentrated cell preparation. Additionally, the presence of CD14+ monocytes that express low levels of CD4 may affect sample purity. Therefore, the ideal volume of magnetic separation beads requires optimization. High yield (119% compared to standard) was observed in comparison with a typical isolation performed in Eppendorf tubes.

Fluorescently-labeled cells may be enumerated using a spectrophotometer. Two sets of PBMC were identically labeled with anti-CD4-PE antibodies and two-fold serial dilutions were prepared. The cells in one set of dilutions were counted using flow cytometry and the cells in the other set of dilutions were measured on a laboratory spectrophotometer to determine total fluorescence. The two-fold dilutions were found to have a very high $R^2$ value, indicating a high level of accuracy in dilution preparation (FIG. 11A). The cell count comparison also had a good $R^2$ value, but was subject to some variation due to the nature of the indirect comparison—fluorescence vs. a calculated value for cell count (FIG. 11B). The limit of detection was found to be appropriate for detecting about 100-200 cells, which is clinically relevant for both initiation of ART as well as ART maintenance.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

E. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241
Avison, In: *Measuring gene expression*, Taylor & Francis, NY, 2007; 324, 2007.
Beuselinck et al., *J. Clinical Microbiol.*, 43(11):5541-5546, 2055.
Chen et al., *Biomed. Microdevices*, 12(4):705-719, 2010.
Coiras et al., *J. Med. Virol.*, 69(1):132-144, 2003.
Hagan et al., *Lab. Chip.*, 11(5):957-961, 2011.
Handbook of Solvents, Lide (Ed.), CRC Press, 1-565, 1995.
Monteiro et al., *J. Clinical Microbiol.*, 35(4):995-998, 1997.
Niemz et al., *Trends Biotechnol.*, 29(5):240-250, 2011.
Price et al., *Lab. Chip.*, 9(17):2484-2494, 2009.
Radstrom et al., *Mol. Biotechnol.*, 26(2):133-146, 2004.
Wilson, *Appl. Environ. Microbiol.*, 63(10):3741-3751, 1997.
Yamada et al., *J. Virol. Methods*, 27(2):203-209, 1990.

What is claimed is:

1. A method of processing a fluid sample comprising an analyte, the method comprising the steps of:
   (a) providing a device comprising a plurality of sequential chambers connected by tubing, each of said sequential chambers comprising a fluid and separated by plug material that is solid at temperatures below about 45° C., wherein a first reaction chamber of the plurality of sequential chambers comprises a magnetic or paramagnetic particle having a reactant on its surface;
   (b) introducing into said first reaction chamber the fluid sample comprising the analyte;
   (c) incubating said first reaction chamber under conditions sufficient to permit binding of said reactant with said analyte in said sample;
   (d) heating said plug material in said device to a temperature above 45° C., thereby rendering at least a portion of said plug material into a liquid state, thereby forming a surface tension valve, wherein heating is performed by placing a heated magnet in proximity of said plug material;
   (e) transporting said magnetic or paramagnetic particle from said first reaction chamber, into at least a second chamber of said plurality of sequential chambers through tubing disposed therebetween, wherein transporting comprises passing said magnet along said tubing to effect movement of said magnetic or paramagnetic particle; and
   (f) detecting interaction of said analyte with said reactant by determining the presence or absence of said analyte in said second or a subsequent chamber of said plurality of said sequential chambers.

2. The method of claim 1, wherein said plurality of sequential chambers comprises at least three chambers.

3. The method of claim 2, further comprising reversing the transport of said magnetic particle to reintroduce said magnetic or paramagnetic particle into a chamber through which it has already passed.

4. The method of claim 2, wherein said device comprises continuous tubing and multiple plugs separating said tubing into said plurality of sequential chambers.

5. The method of claim 4, wherein said tubing comprises an inner surface coated by a polymer.

6. The method of claim 1, wherein said magnetic or paramagnetic particle has a relative density of >1 or <1 compared to the sample fluid.

7. The method of claim 1, wherein step (d) takes place after step (a) but before step (b).

8. The method of claim 1, wherein step (d) takes place after step (b) but before step (c).

9. The method of claim 1, wherein step (d) takes place after step (c).

10. The method of claim 1, wherein said particle is the magnetic particle.

11. A method of processing an analyte-containing sample comprising:
   (a) providing a device comprising a plurality of sequential chambers connected by tubing, each of said sequential chambers comprising a fluid and separated by a plug material that is solid at a temperature of less than 45° C.;
   (b) introducing into a first chamber of said plurality of sequential chambers a magnetic or paramagnetic particle comprising a surface reactant disposed in a fluid, wherein an analyte is bound to said surface reactant;
   (c) heating said plug material in said device to a temperature above 45° C., thereby rendering at least a portion of said plug material into a liquid state, thereby forming a surface tension valve, wherein heating is performed by placing a heated magnet in proximity of said plug material;
   (d) transporting said magnetic or paramagnetic particle from said first chamber of said plurality of sequential chambers into at least a second chamber of said plurality of sequential chambers through tubing disposed therebetween, wherein transporting comprises passing said magnet along said tubing to effect movement of said magnetic particle; and
   (e) detecting the presence of said analyte by determining the presence or absence of said analyte in said second or a subsequent chamber of said plurality of said sequential chambers.

12. The method of claim 11, further comprising, prior to step (b), the step of mixing said magnetic or paramagnetic particle with said analyte-containing sample to permit binding of said analyte to said surface reactant on said magnetic particle.

13. The method of claim 11, wherein said magnetic or paramagnetic particle has a relative density of >1 or <1 compared to the fluid.

14. The method of claim 11, wherein said plurality of sequential chambers comprises at least three chambers.

15. The method of claim 14, further comprising reversing the transport of said magnetic particle to reintroduce said magnetic or paramagnetic particle into a chamber through which it has already passed.

16. The method of claim 11, wherein step (c) takes place after step (a) but before step (b).

17. The method of claim 11, wherein step (c) takes place after step (b).

18. The method of claim 11, wherein said particle is the magnetic particle.

* * * * *

SEQUENCE LISTING

<160> NUMBER OF SEQ ID NOS: 2

<210> SEQ ID NO 1
<211> LENGTH: 22
<212> TYPE: DNA

```
<213> ORGANISM: Artificial sequence
<220> FEATURE:
<223> OTHER INFORMATION: Synthetic primer

<400> SEQUENCE: 1
accagcacct aaccggctgt gg                                              22

<210> SEQ ID NO 2
<211> LENGTH: 22
<212> TYPE: DNA
<213> ORGANISM: Artificial sequence
<220> FEATURE:
<223> OTHER INFORMATION: Synthetic primer

<400> SEQUENCE: 2
catcgtggaa gcgacccgcc ag                                              22
```